United States Patent [19]

Giaever

[11] 4,041,146

[45] Aug. 9, 1977

[54] METHOD FOR DETECTION OF BIOLOGICAL PARTICLES

[75] Inventor: Ivar Giaever, Schenectady, N.Y.

[73] Assignee: General Electric Company, Schenectady, N.Y.

[21] Appl. No.: 573,610

[22] Filed: May 1, 1975

[51] Int. Cl.$^2$ .................. G01N 33/00; G01N 33/16; A61K 43/00
[52] U.S. Cl. ..................................... 424/1; 23/230 B; 424/12; 424/7
[58] Field of Search ................... 23/230 B; 424/1, 1.5, 424/7, 12

[56] References Cited

U.S. PATENT DOCUMENTS

| | | | |
|---|---|---|---|
| 3,284,434 | 11/1966 | Sutherland et al. | 424/12 X |
| 3,555,143 | 1/1971 | Axen et al. | 424/1 |
| 3,592,888 | 7/1971 | Wolf | 424/1 |
| 3,639,559 | 2/1972 | Tax | 424/12 |
| 3,720,760 | 3/1973 | Bennich et al. | 424/1.5 X |
| 3,826,619 | 7/1974 | Bratu, Jr. et al. | 23/253 R |
| 3,896,217 | 7/1975 | Johnson | 424/1 |
| 3,979,509 | 9/1976 | Giaever | 424/12 |

OTHER PUBLICATIONS

Chidlow et al, Biochem. Journal (Great Britian), vol. 117, 1970, pp. 49–55.

*Primary Examiner*—Benjamin R. Padgett
*Assistant Examiner*—Christine M. Nucker
*Attorney, Agent, or Firm*—Leo I. MaLossi; Joseph T. Cohen; Jerome C. Squillaro

[57] ABSTRACT

A monomolecular layer of first biological particles is absorbed on the surface of a non-reactive substrate. The coated substrate is exposed to a solution suspected of containing second biological particles specific to the first biological particles. Next, the coated substrate is subjected to a tagging step, following which it is exposed to a cleaving agent solution which cleaves the bond between the first and second biological particles. The used cleaving agent solution is then examined by a tag-sensing instrument following possible concentration thereof for determining whether tag-bearing second particles have been removed. The tags may, for example, be radioactive, fluorescent, etc. A supplement is described, wherein the coated substrate is studied with a tag-sensing instrument before and after exposure of the coated substrate to the cleaving agent solution to help provide said determination.

31 Claims, 7 Drawing Figures

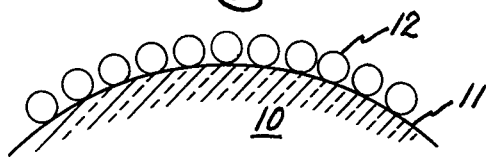
Fig. 1.
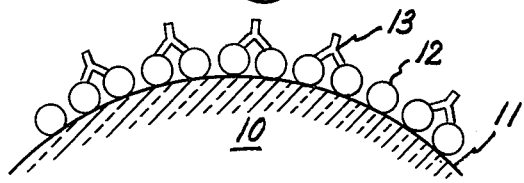
Fig. 2.
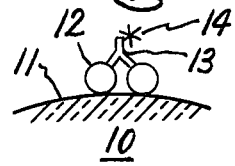
Fig. 3.a.
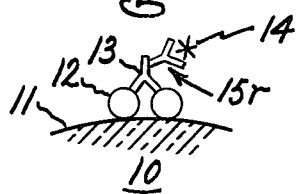
Fig. 3.b.
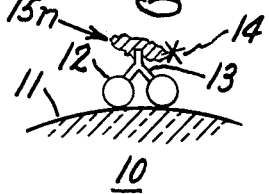
Fig. 3.c.
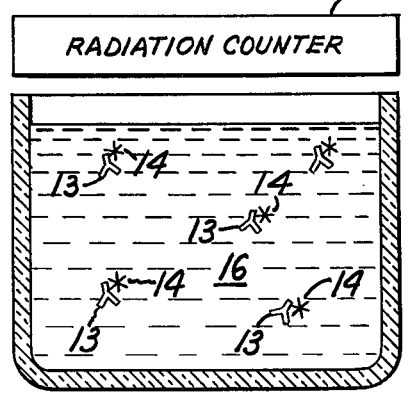
Fig. 4.
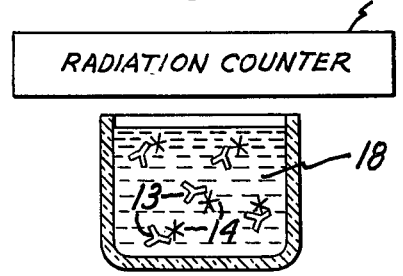
Fig. 5.

METHOD FOR DETECTION OF BIOLOGICAL PARTICLES

This invention relates to a medical diagnostic method and apparatus for detecting immunologic (as well as other specific) reactions occurring on the surface of a solid, non-reactive substrate. In particular, the method is one wherein first reactive particles are attached to the substrate and after an opportunity has been provided for a specific reaction of the first particles with second particles, should they be present, to occur upon the substrate, a tagging operation is conducted. The tagging operation is followed by a cleaving operation for cleaving the tagged second particles, if present, from the first particles, the used cleaving agent being studied with a tag-sensing instrument. Alternatively, the substrate may be studied with the tag-sensing instrument before and after the cleaving operation, for initial presence then disappearance (or substantial reduction) of tags.

This application is related to my copending U.S. Patent applications Ser. No. 266,278 (now abandoned) entitled "Method and Apparatus for Detection and Purification of Proteins and Antibodies" filed June 26, 1972; continuation-in-part application Ser. No. 384,113 (now abandoned) entitled "Improved Method and Apparatus for Detection and Purification of Proteins and Antibodies" filed July 30, 1973; (now U.S. Pat. No. 3,926,564) entitled "Improved Substrate for Immunological Tests and Method of Fabrication Thereof" filed Feb. 25, 1974; Ser. No. 430,884 (now abandoned) entitled "Method and Apparatus for Surface Immunological Detection of Biological Particles by Radioimmunoassay" filed Jan. 4, 1974; and Ser. No. 503,030 (now U.S. Pat. No. 3,979,509) entitled "Opaque Layer Method and Apparatus for Detecting Biological Particles", filed Sept. 3, 1974 and to U.S. Pat. application Ser. No. 388,407 (now U.S. Pat. No. 3,904,367) entitled "Contrast Enhancement for Immunological Film Detection", inventor Golibersuch, filed Aug. 15, 1973, each application assigned as herein.

A related, commonly assigned patent, based on a prior application of mine is U.S. Pat. No. 3,853,467, issued Dec. 10, 1974, upon application Ser. No. 388,406, entitled "Method and Apparatus for Immunological Detection of Biological Particles", filed Aug. 15, 1973.

Other publications related to the present invention primarily as background are "The Antibody-Antigen Reaction: A Visual Observation", Ivar Giaever, *The Journal of Immunology*, Vol. 110, No. 4 (May 1973), pages 1424–1426 and "Three Simple Ways to Detect Antibody-Antigen Complex on Flat Surfaces", A. L. Adams et al., *Journal of Immunological Methods*, Vol. 3, (1973), pages 227–232 and U.S. Pat. No. 3,853,987, entitled "Immunological Reagent and Radioimmunoassay", issued Dec. 10, 1974 to William J. Dreyer, upon application Ser. No. 177,017, filed Sept. 1, 1971.

The term "biological particle" is intended to encompass smaller proteins (e.g. plasma proteins, antigens, antibodies, lactins) and bodies of proteinaceous material (e.g. viruses, bacteria, cells) capable of stimulating antibody production, when injected into an animal, and/or having the property of interacting specifically either immunologically or non-immunologically.

The term "tag" as used herein refers to an identifying molecule or group of atoms from which emanations occur, a. which can be chemically integrated into an entity that is itself difficult or presently impossible to detect in dilute concentrations and b. which, because of emanations therefrom, can be detected even in very small quantities by the use of appropriate instrumentation.

Recognition of the tag (e.g. radioactive isotope, fluorescent group) automatically identifies the presence of the entity into which it is integrated.

Immunological reactions are highly specific biophysical reactions in which a first immunologically reactive biological particle known as the antigen combines (links) with a second reactive biological particle specific to the antigen, and known as the antibody, to form an immunologically complexed protein. Immunological reactions taking place within a biological system such as an animal or human being are vital in combatting disease. In a biological system, the entry of a foreign protein, i.e., the antigen, causes the biological system to produce antibody proteins specific to the antigen in a process not fully understood at this time. However, some of the most important antibodies used in diagnostic reactions are not related to the entry into a biological system of any known foreign molecule. Some antibodies, such as anti-A and anti-B used in blood grouping, are called natural antibodies, because they are found in human sera apparently without the requirement of prior antigenic stimulation. Other antibodies seem to have the ability to react with some constituents normally present in the body. This leads to the pathological condition known as autoimmunity or autoallergy. Examples of such antibodies include the antinuclear antibodies of systemic lupus erythmatosus, the rheumatoid factors of rheumatoid arthritis, and the anti-thyroglobulin antibodies of chronic thyroiditis (Hashimoto's Disease). The antibody protein molecules have available combining or binding sites which complement those of the antigen molecule so that the antigen and antibody physically link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. The above-cited copending applications disclose that an arbitrary protein will adhere to a substrate in a monomolecular layer only, and that no other arbitrary protein will adhere to the protein layer. On the other hand, the specifically reacting protein to the first protein adsorbed onto the substrate will immunologically bond thereto. In accordance with the teachings and objectives of those applications, this phenomenon is exploited to provide medical diagnostic apparatus in which a particularly prepared slide having a monomolecular layer of one protein adsorbed thereon is used to test suspected solutions for the presence or absence of the specifically reacting protein thereto. If the specifically reacting protein is present in the solution, the slide after exposure to the solution has a bimolecular protein layer thereon. If the specifically reacting protein is absent from the solution, the slide after exposure to the solution has only the original monomolecular protein thereon. The use of various optical, electrical, chemical and radioactive means for distinguishing between bimolecular and monomolecular biological particle layers are taught in the related copending applications and have different degrees of sensitivity and economy. Examination of the protein coated slide with the unaided eye is the preferred approach for determining the number of biological particle layers on the slide due to its simplicity and some of the above-identified copending patent applications teach such an approach.

The detection of antibodies in a biological system is of medical diagnostic value in determining the antigens to which the system has been exposed. An example of diagnostic detection of antibodies is the detection of antibodies to syphilis or gonorrhea in human serum. Conversely, the detection of certain antigens in a biological system also has medical diagnostic value; examples of diagnostic detection of antigens include detection of HCG-protein molecules in urine as a test for pregnancy, and detection of hepatitis-associated-antigen (HAA) molecules in the blood of prospective blood donors.

In order to perform such diagnostic tests, the appropriate protein of the immumologically reacting pair must be obtained. At present, the source of an antibody protein must be a living biological system. More particularly, vertebrates are known to exhibit immunological reactions to the introduction of a foreign protein. For example, many antibodies are found in the blood serum of animals and human beings which have been exposed to the corresponding antigens. Invertebrates may also exhibit immunological reactions, although they probably do not have specific memory. Even some plant proteins combine with antigens and these so-called lectins may be of considerable use in diagnostic reactions. Some antigens may be controllably produced in laboratory cultures. However, most antigens, for example, hepatitis-associated-antigens, are at present, like antibodies, only obtainable from higher biological systems and thus many antigens are obtained from natural sources such as human or animal tissues.

It is known in the immunological art that antibody molecules function as antigens when introduced into the system of a vertebrate to whom they are foreign proteins. Accordingly, specifically reacting antibodies to a given antibody may be produced in such vertebrate system.

Although the emphasis herein will be on biological particles that immunologically react with each other, my invention also includes other forms of biological interactions between large molecules based on nonimmunological specifications such as for example, the binding of enzymes to their biological substrates, or hemoglobin to haptoglobin.

It is also known in the immunological art to attach a first biological particle such as an antigen (or antibody) to a solid surface, to expose the attached first particle to a solution suspected of containing a second biological particle to which the first particle is specific, and then to expose the system to a radioactive-tagged antibody to the second particle. The above technique is utilized to detect hepatitis by initially coating the inner bottom surface of a test tube with antibodies to HAA, then adding a blood sample suspected of containing HAA and finally adding a radioactively-tagged antibody to HAA. A radiation counter is then used to test the total bottom surface of the test tube for radioactivity.

It is known in the immunological arts to prepare antibodies to human immunoglobulins for chemical combination with fluorescent organic molecules such as the isothiocyanates. This tagged antibody is then used to render an immunological reaction visible by ultraviolet microscopy, particularly in the serological test for syphilis after the method of Coons, now known in the art as FTA-STS procedure. In the FTA-STS procedure, a quantity of Treponema pallidum (T. pallidum) is dried on a slide. The slide is then immersed in a blood specimen. The slide is subsequently immersed in a solution of tagged immunoglobulin. The anti-human immunoglobulin does not bond to the T. pallidum; accordingly, the slide will fluoresce, when observed by ultraviolet microscopy only if the specimen contained antibodies to T. pallidum.

In my above-mentioned co-pending application, Ser. No. 430,884, the detection of immunologically reactive biological particles such as viruses, bacteria and other cells is obtained by determining whether an immunological reaction occurs on a substrate between the particle to be detected and its radioactive-tagged antibody. A monomolecular layer of first immunologically reactive biological particles is adsorbed onto the surface of the substrate in a distinct pattern, and the substrate is then exposed to a solution suspected of containing the particles to be detected, which particles are specific to the first particle. The substrate is exposed to the radioactive-tagged antibody to the particle to be detected and, finally, the substrate surface is monitored for radioactivity. If the particle to be detected was present, the distinct pattern will emit a significantly higher radiation level than the surrounding substrate.

In my above-mentioned co-pending application, Ser. No. 503,030, a method is described in which a monomolecular layer of first biological particles is adsorbed on the surface of a substrate fabricated of virtually any nonreactive solid material; the coated substrate is then exposed to a solution suspected of containing second biological particles specific to the first biological particles; next a porous, opaque layer of nonreactive third particles is formed on the coated substrate, and then the coated substrate is exposed to a cleaving agent solution which cleaves the bond between the first and second biological particles. A visual examination of the coated substrate surface or examination thereof by suitable instrumentation is made, to determine whether the suspect solution contains the second biological particles by discerning whether the opaque layer is complete or whether a portion common to the second biological particles, has been removed.

Still, there are instances in which the reaction proceeds so slowly, or wherein so few of the second particles are present in the specimen that the second layer, while present, is sparse and difficult to detect by optical means.

Thus, a method which can improve the contrast of a search by tag-sensing without requiring a prolonged reaction time is much sought and such is an object of this invention.

In contrast to prior teachings, wherein the tag-sensing instruments are used to examine a protein-coated surface for the presence of a pre-tagged second protein, secured to the first protein, the present invention provides a process wherein second biological particles (untagged) are permitted, if present in the specimen, to complex with first biological particles attached to a substrate and thereafter tagging is accomplished. Next, the system is contacted with a solution of cleaving agent to sever the bond securing the two layers of biological particles to one another. The used cleaving agent solution is collected and investigated for presence of tags therein, which would establish the presence of the second biological particles.

The presently preferred tags are radioactive ones, for instance, iodine 125 (designated I - 125 or $^{125}$I).

The tags can be applied in at least these ways:

a. Second biological particles may be tagged directly, after a layer thereof has become secured to the first layer taking care not to prematurely separate the first layer from the substrate. (Also, if some of the first layer becomes tagged during performance of the tagging operation, a consistent result may still be obtained from a tag sensing study of the solution of used cleaving agent, because the cleaving agent does not remove the first layer and its tags would still be attached to the substrate.)

This preferred mode of tagging can reduce expenses of operation while improving contrast. Pre-tagged biological particles are expensive and have a short half-life. They may also be less reactive towards the first biological particles than the untagged biological particles from which they were made would have been. One currently marketed test kit for Hepatitis Associated Antigen which includes $^{125}$iodine pre-tagged third layer Hepatitis Associated Antibody bears a shelf life of 28 days.

b. The second biological particles may be tagged after the securing thereof to the first layer, by the application of any pre-tagged non-biological material which will adhere to the second protein sufficiently to form a uniformly distributed coating thereover sufficiently porous to permit the cleaving agent solution to readily diffuse therethrough. While the cleaving agent is to sever the bond between the second and first layers of biological particles it must not significantly disturb the adherence of the pre-tagged adhering material to the first layer. The pre-tagged adhering material, which is carried from the surface in the cleaving agent solution provides a reliable indicator of the presence or absence of the second biological particles.

Tagging methods (a) and (b) are clearly preferred, because the drawbacks associated with pre-tagged biological particles are avoided. These drawbacks are a shortened operating life span (depending on the length of time the tag is effective), reducing the number of active sites on the biological particles and actual loss of the biological particles (before complexing) from radiation or other adverse effects.

c. Second biological particles may be tagged indirectly by contacting the coated substrate, following its exposure to a specimen possibly containing the second protein, to a solution of pre-tagged third biological particles, specific to the second but not to the first wherein, as in the instance of hepatitis, such a system exists. Then, by subjecting the coated surface to a cleaving agent, the bond between the first and second and/or the second and third layers is severed and the used cleaving agent solution is subjected to the tag-sensing operation.

In any of the above-identified ways of tagging, the coated surface may also be studied with the tag-sensing means before and/or after the cleaving step has been conducted, in order to provide checks, measures of background and the like.

It is an important object of the invention to provide a method of the type described, wherein a used cleavage agent solution containing tags in a lower concentration than could be readily or reliably detected, may be concentrated prior to being subjected to the tag-sensing step. For conducting the process of the invention, the substrate surface need not be flat, and may be of as great an area as economical use of the process will permit in order to increase the probability that more second particles will become secured to the first layer within a reasonably brief test period.

(Tests which may be conducted and the results determined (a) while an operative procedure is in progress or (b) over night, are most desired.)

The features of my invention which I desire to protect herein are pointed out with particularity in the appended claims.

The invention itself, however, both as to its organization and method of operation together with further objects and advantages thereof, may best be understood by reference to the following description taken in connection with the accompanying drawings wherein:

FIG. 1 is a schematic elevation view in cross-section through a portion of a substrate having adsorbed thereon a monomolecular layer of first biological particles;

FIG. 2 is a schematic elevation view in cross-section of the coated substrate of FIG. 1 following contact thereof with a specimen containing a second biological particle, which is specific to the first and has formed a second monomolecular layer thereupon;

FIGS. 3a, 3b, and 3c schematically show individual second biological particles tagged in three respectively different ways following securement thereof in the untagged state to the first biological particles of the first layer;

FIG. 4 is an elevation view in section depicting the detection step applying tag-sensing means to the cleaving agent solution and rinsing liquid collected following the cleaving step; and FIG. 5 is an elevation view, similar to FIG. 4 depicting the detection step after concentration, as by evaporation, of the cleaving agent solution and rinsing liquid of FIG. 4.

Referring now to FIG. 1, there is shown schematically in cross-section at the surface a typical substrate 10 that may be utilized in my method for detecting an immunologic or other specific reaction involving biological particles. The substrate 10 may be fabricated of virtually any solid material that is nonreactive with the biological particles, cleaving agent solution and other materials used with the substrate in the conduct of the method. The surface 11 of substrate 10 must be impermeable and non-absorbent to the solutions of biological particles, tags and cleaving agent used in the method and must permit the adsorption of a monomolecular layer of the first biological particles thereon. The surface 11 need be neither light transmitting nor flat. Although the substrate could be constituted by a plain glass slide, this is not the preferred material, due to a tendency for cleaving agent solution to desorb too many first biological particles therefrom. Preferred and useful materials include a plurality of small spheres (e.g. about 25 mm. total surface area) presenting a thin tenacious, non-porous surface of gold, chromium, tantalum or molybdenum, by way of example. Slides, rods, glass container, internal surfaces and the like are alternatives for use as the substrate.

The size of the substrate 10 is governed primarily by the cost of materials consumed in the test, compared to the cost of time for conducting the test. Enlarging the area of the surface may increase the cost of the materials, but decrease the contact time needed to produce a collection of tags that is sufficiently concentrated to be clearly distinguished by the tag-sensing means.

The surface 11 must be free of any contaminants, such as cleaning solution residue, which might prevent or impede adsorption of the first monolayer of biological particles thereon.

Having selected a suitable substrate 10 having a thoroughly clean surface 11, a monomolecular layer 12 of first biological particles is adsorbed thereon. The identity of the material 12 will vary with the particular test being conducted. Bovine serum albumin is exemplary of a material comprising first biological particles.

While the emphasis herein will be on immunologically reactive biological particles (the simplest case being the antigen-antibody pair), for the purposes of simplicity and exemplification, it should be understood as explained at the outset that my invention is equally useful with sets of biological particles that undergo forms of biological interaction other than an immunologic reaction, the only criterion being that the particles are mutually specific.

The adherence of the first biological particles as a monomolecular layer may be accomplished by depositing one or more drops of a solution of the first biological particles on the surface 11 using a dropper or other means. Alternatively, the substrate 10 may be dipped into a solution of the first biological particles. The first biological particles are selected on the basis of being specifically reactive to particular second biological particles, which will form a second layer on the substrate surface, if they are present in a second solution, or sample thereof, to be tested.

The first biological particles may be produced in laboratory cultures or obtained from the higher living biological systems as described hrereinabove, and are generally commercially available in a relatively highly purified form, and if not available commercially, may be purified chemically. The solution of the first biological particles may be a salt solution of water or other liquid appropriate to, and not reactive with, the first biological particles and the substrate material. A more detailed description of the formation of the first (and second) particle monolayers in all the embodiments of my present invention is included in the teachings of the aforementioned copending U.S. patent applications of Giaever, which are herein incorporated by reference.

The time interval (generally up to one hour) for the formation of the first monomolecular layer 12 on substrate surface 11 is an inverse function of the concentration of the first biological particles in the first solution. The first monomolecular layer 12 covers substantially the entire surface 11 of the substrate 10 and substrate 10 is, therefore, made as small as practical in order to conserve the amount of biological material used in the process, yet sufficiently large to permit the test to be conducted reliably within a short time. A rinsing of the monomolecular layer coated surface of substrate 10 with tap water or distilled water is recommended in order to remove excess first biological particles (and possibly others existing in the first solution) that may accumulate on top of monolayer 12.

The monolayer-coated substrate 10 is then dried, if the substrate is to be shipped commercially or stored, preferably by blowing air at room temperature across the substrate in order to speed the drying process. If the substrate is to be used immediately, there is no need to dry it after the rinsing. The first monomolecular layer 12 is generally invisible to the unaided eye since the thickness of such monomolecular layer may be anywhere from 20 to 100 Angstroms, depending on the particular biological particle forming such layer.

Referring now to FIG. 2, the monolayer-coated substrate is next exposed to a second solution, or sample thereof, suspected of containing the second immunologically reactive biological particles that are specific to the first biological particles in a direct test for such second particles. This exposure is generally accomplished by immersing the monolayer-coated substrate in the second solution for a time interval, which is again an inverse function of the concentration (usually unknown) of the second biological particles in the second solution. Since the concentration of the second particles in the second solution is generally much less than the concentration of first particles in the first solution, the immersion step generally takes much longer than the time interval for forming the first biological particle monolayer 12, and may take up to 24 hours. The time can be shortened if a larger-area surface 11 is used.

Presence of the second biological particles in the second (test or suspect) solution will result in the formation of a second substantially complete monomolecular layer 13 over layer 12 as a result of the biophysical reaction between the second biological particles and the first biological particles. After the monolayer-coated substrate has been sufficiently exposed to the second solution, the coated substrate is removed therefrom and is rinsed with tap water, distilled water or a dilute salt solution depending upon the nature of the solution in which the second biological particles were contained. This rinsing step is utilized to prevent an excess build-up of the second biological particles on the substrate as well as to minimize non-specific absorption (i.e. the second solution is typically a complex, unseparated serum containing a great number of other type biological particles. The coated substrate may then be dried in a manner described hereinabove, if required for optional subsequent treatment described hereinbelow. If second biological particles are not present in the second solution, no deposition of a second monomolecular layer occurs over layer 12.

After the second monomolecular layer 13 has formed on the coated substrate, the second biological particles may be directly tagged as illustrated at 14, FIG. 3a. Radioactive tagging is preferred. A method for radioiodination of particles is described by W. M. Hunter and F. C. Greenwood (*Nature,* 194 (1962) page 495).

The tagging should be carried out in neutral solution in order to avoid premature separation of the second layer, if it exists, from the first layer. Suitable methods for radioactively tagging an anchored layer of biological particles are thoroughly described in *Handbook of Experimental Immunology* [Ed. D. M. Weir, Blackwell Scientific Publications (1973)] Chapter 17 "Radioimmunoassay" by W. M. Hunter pp. 17.1–17.36 and in references cited therein. Direction to the technician is also provided in *Principles of Competitive Protein-Binding Assays* [Ed. W. D. Odell & W. H. Daughaday. Philadelphia: Lippincott (1971)] in Chapter X "Radioiodination of Peptide Hormones: Procedure and Problems" by F. C. Greenwood pp. 288–296. Another reference work which describes suitable radioactive tagging methods is in *Radioimmunoassay Methods* [Ed. K. E. Kirkham & W. M. Hunter, Churchill: Livingstone (1971)] "The Preparation and Assessment of Iodinated Antigens" by W. M. Hunter pp. 3–23 and "The Immuradiometric Assay" by G. M. Addison and C. N. Hales pp. 447–461.

Fluorescent tagging is an alternative to radioactive tagging and others will occur to those skilled in the art. The procedure for fluorescent tagging as well as radioactive tagging are generally understood by those skilled in the art. Suitable methods for fluorescent tagging of an anchored layer of biological particles are thoroughly described in the aforementioned *Handbook of Experimental Immunology* in Chapter 18 "Immunofluorescence" by G. D. Johnson and E. J. Holborow.

The aforementioned publications describing tagging techniques are incorporated by reference.

As an alternative to direct tagging of the second biological particles, as depicted in FIG. 3a, the second biological particles may be indirectly tagged, by pretagging third particles 15r bearing tag 14, particles 15r being known to be specific to the second biological particles, but not specific to the first biological particles. These tagged particles are used to form a third layer upon the monomolecular layer of second biological particles. This alternative is depicted in FIG. 3b. The third particles are first tagged as described above for the embodiment of FIG. 3a. The tagging of the third particles is also preferably radioactive, being exemplified by being iodinized with $^{125}$I.

Thus, in greater detail, after the coated substrate 10 of FIG. 3b has been sufficiently exposed to the second biological particles in solution, the substrate is removed from the second solution suspected of containing such particles and is washed by a suitable solution (e.g. water or a dilute aqueous salt solution) in order to remove most of the non-specific particles stuck to the substrate. The coated substrate is subsequently exposed to a solution of third biological particles 15r which are radioactively-tagged and are biophysically reactive with the second biological particle, for example, an antibody to the second biological particle. In any event, the radioactive-tagged third biological particle is specific to the second biological particle so that presence of the latter on substrate 10 causes the third particles to complex therewith and form a third monomolecular layer on substrate 10 over the previously deposited monomolecular layers, as illustrated in FIG. 3b. The exposure of coated substrate 10 to the third biological particles can be accomplished by immersion in a third solution of such particles or by being coated with the third solution in the case of a sufficiently high concentration thereof. Again, the length of the exposure of the substrate to the third solution required in order to obtain a substantially complete layer of third particles 15r upon the layer of second biological particles, is primarily a function of the concentration of such particles in the third solution. The concentration of the third particles can be controlled, as in the case of the first particles, since these particles are produced in laboratory cultures or in the higher living biological systems. The concentration of these biological particles is generally much higher than the concentration of the second particles in the second solution so that the time interval of exposure to the third particles is generally much less than the immersion in the second solution.

A third alternative is depicted in FIG. 3c wherein the second biological particles of the second layer are tagged, after the layer of second biological particles has become affixed, by the deposition thereon (and on any still exposed part of the first layer) of a layer or coating of third particles 15n. The layer of third particles 15n is characterized by being nonreactive with substrate 10 and with the biological particles forming monolayers 11 and 12, by being pre-tagged (for instance, radioactively-tagged with $^{125}$I) and by being deposited over the entire coated surface of the substrate to form the third and outermost layer. In the case in which the second solution did not contain second biological particles, layer 15n forms only the second layer on substrate 10. Nonreactive layer 15n must be sufficiently porous so that subsequent exposure of the coated substrate to a cleaving agent solution permits the cleaving agent to penetrate layer 13 as will be described hereinafter. Because of the subsequent exposure to the cleaving agent solution, particles 15n of the third layer must also be nonreactive with the cleaving agent.

The layer of particles 15n may be formed of virtually any material that exists in discrete small particle form and can be dispersed in a porous continuous layer, that can be pre-tagged using known techniques, that will adhere to the biological particle layers already deposited and that are nonreactive with the first and second biological particles, substrate and cleaving agent solution.

Thus, the third layer may be formed by dipping the coated substrate into an agitated third solution containing a relatively high concentration of such pre-tagged nonreactive particles so as to form a layer of the particles 15n in contact with each other or in slightly spaced apart relationship. Metal, glass or plastic pre-tagged particles in a suitable agitated solution may also be utilized to obtain layer 15n. The solution in which the metal, glass or plastic particles are contained may simply be water. In the case wherein the coated substrate is dipped into a solution of the small particles, there is no need to dry the coated substrate after the exposure of the monolayer-coated substrate to the solution suspected of containing the second biological particles and rinsing thereof, because the solution containing particles 15n will moisten the coated substrate. The size of the generally spherical third particles 15n, whether they be of glass or plastic, can be over a wide range of values (diameters of 0.1 to 100 micrometers) since the function of layer 15n is merely to present a tagged porous layer to the cleaving agent solution to be utilized hereinafter.

An alternative method for applying the third layer of particles 15n on the substrate is to utilize a conventional aerosol spray can filled with virtually any material nonreactive with the substrate, biological particles and cleaving agent, properly tagged and formative of a porous layer, preferably opaque. The coated substrate should be in a dry condition prior to this spraying process in order to obtain more efficient sticking of particles 15n to layer 13 (or 12). The particles suspended in a gas to constitute the aerosol may either be finely-divided solid or liquid. As a typical example, the dried, coated surface of the substrate may be lightly sprayed with modified MS-122 FLUORCARBON, a release agent and dry lubricant product of Miller-Stephenson Chemical Company. This product normally consists of an aerosol preparation of a low molecular weight synthetic resin polymer wax. For use in the present invention, prior to being packaged, the polymer particles are uniformly coated with a hydrocarbon, oil-based (water-insoluble) solution of e.g., a radioactively iodinated inorganic iodine salt. The tags may be physically trapped in, dispersed in, adsorbed on or chemically bound to the particulate carriers therefore.

If the layer 15n is made of material of high contrast, for instance, the tagged fluorocarbon wax aerosol, the extent of homogeneity of the distribution of tags can also be optically checked. If optical checking is not feasible or is not comtemplated, the layer 15n need not comprise a highly visible carrier material such as tagged fluorocarbon wax, but may consist of e.g., a hydrocarbon oil-based (water insoluble) solution of a radioactively iodinated inorganic iodine salt.

The thickness of the sprayed-on layer 15n may be substantially greater than the thickness of monomolecular layers 12 and 13, and is typically in the range of 1 to 10 micrometers, but can be in a range as great as monomolecular to 100 micrometers. The ranges for the discrete particle sizes or sprayed-on layer thicknesses may be different for different materials due to the different porosity and opaqueness thereof.

After the tagging step has been performed, e.g., in accordance with the discussion of FIGS. 3a-3c above, the coated surface of substrate 10 is exposed e.g. drops to a cleaving agent solution such as a weak acid solution, alkaline solution, or a solution containing a concentration of salt. Since the layer 13, if present, and any subsequently deposited layer are porous, the cleaving agent penetrates to the monomolecular layer of first biological particles, and, if the second biological particles are present, cleaves the bond between the first and second biological particles, but not the bond between the first biological particles and the substrate. Monomolecular layer 13 is removed from the region in which cleavage occurs being carried in the cleaving agent solution 16 (and in the rinsing fluid used). The detached second biological particles and the liquid are collected in a container along with (in the case of the alternatives shown in FIGS. 3b and 3c) the particles 15r or 15n attached thereto.

In the event that the specimen being tested for the presence or absence of second biological particles is free of second biological particle content, application of the cleaving agent solution to coating on the surface 11 has no effect on the coated surface of the substrate and tags are not collected in the cleaving agent solution beyond a small, background amount. Further, in this event when the alternate method illustrated in FIG. 3c is used, the layer consisting of particles 15n will remain complete during conduct of the cleaving, rinsing and collecting steps.

In the case of the cleaving agent being an acid solution, the acid solution utilized is generally a weak one, that is, it is sufficiently strong enough to cleave the bond between layers of first and second biological particles, but not strong enough to cleave or otherwise affect the bond between the first layer 12 of biological particles and the solid surface of substrate 10 to which it is adsorbed. A 0.1 normal (N) citric acid solution is suitable for the purposes herein described. The range of concentrations of the citric acid for obtaining the desired results are approximately 0.01 to 1.0 N. Other suitable weak acids that may be utilized are 0.1 N malic acid and 0.1 N formic acid. Stronger acids such as hydrochloric acid and sulfuric acid may also be utilized, but in a much smaller concentration (i.e., approximately 0.01 N). The weak acid solution that may be utilized in my invention may be generally described as being any acid solution that does not attack the substrate or any third layer material to be applied and, preferably has a pH in a range between 2 and 5, although a pH as low as 1.0 was found to be satisfactory (using 0.1 N hydrochloric acid).

As noted hereinabove, alkaline and high salt concentration solutions may also be used as cleaving agents. The alkaline solution useful herein has a pH in the range 9–13, and typically, a 0.2 N sodium hydroxide solution has been used to cleave the bond between egg albumin and its antigen. Various salt solutions of elevated salt concentration, such as NaCl and NaI are known to function as cleaving agents. Thus, a 1.79 molar NaCl solution cleaves pneumococcal polysaccharide from its antibody.

When, for example, radiation tagging is employed, the autoradiography technique may be used to detect radiation emission by the use of special photographic film sensitive to gamma rays, this film being placed in proximity to the used cleaving agent solution. The presence of gamma radiating tags in the solution becomes readily apparent on such film in view of the much higher level of exposure as compared to the background exposure level. In the case radioactive-tagged third biological particles have been used (FIG. 3b) emitting primarily gamma rays, the radiation counter 17 may be a conventional gamma ray counter comprising a tubing having a scintillator crystal at the aperture end thereof and a photocathode at the output end. The tubing, crystal and voltage bias connections in the counter, being conventional, are not shown. The scintillator crystal, which may be fabricated of sodium iodide as one example, is responsive to gamma rays impinging thereon, and emits light photons which are detected by a photocathode (not shown) and are converted to voltage pulses corresponding to the number of counts detected. The output voltage from the photocathode is conducted to a suitable electronic amplifier (not shown) for amplifying the voltage count pulses. The output of the amplifier is applied to the input of a suitable real-time read-out device (not shown) to provide a visual (oscilloscope) or audible (loudspeaker) output or may be a memory storage device such as magnetic tape for permitting a delayed read-out.

In case the radioactive-tagging employed is such that beta rays are emitted from the tagged entities, the tag-sensing means 17, e.g. a radiation counter may be a conventional beta ray counter comprising a sealed tubing which is gas-filled and has an electrode (not shown) therein connected to a source (not shown) of relatively high voltage such that the beta rays ionize the gas and each gas ionization event is detected by an electronic amplifier (not shown) and read-out device (not shown).

One advantage provided by the method of the invention is that when the tags 14, no matter what their type or affiliation, are in such low concentration in the bulk of the used cleaving agent solution 16 that the tag-sensing device 17 cannot provide a reliable reading, the solution 16 may be concentrated to a smaller bulk 18, thereby concentrating the tags 14 for more reliable detection by the tag-sensing device 17.

If desired, as a check upon the measurement made in FIGS. 4 or 5, the coated substrate may be subjected to study by the tag-sensing means 17 (using substantially the same instrumentation and techniques as have been described above) both prior to and after conduct of the cleaving and rinsing operations to determine any differential read-out.

In the description of my invention hereinabove, reference has been made to first and second immunologically reactive biological particles wherein the second biological particle is specific to the first. The use of this language is deliberate and the immunologically reactive antigen biological particles that may be utilized, and detected, with my invention are meant to include hormones, viruses, bacteria, enzymes and other particles which can be readily grown or otherwise isolated and collected or are present in human serum or other solution being tested. However, my invention is further useful with virtually any pair of biological particles that will physically react (combine) with each other. That is, in addition to being applicable to immunologically reactive antigen-antibody systems, my invention also includes other forms of biological interactions between large molecules based on non-immunological specificities, such as for example, the binding of enzymes to their biological substrates, or the binding of hemoglobin to haptoglobin.

The solution suspected of containing second particles is generally a human serum sample, although it can be another type of solution appropriate to the particular biological particle being investigated. In direct testing wherein it is sought to detect an antibody, such as in the case of syphilis or gonorrhea, the antibody is detected in the human serum of a patient. Alternatively, in the inhibition test to detect an antigen, e.g. hepatitis HAA, the antibody may be developed in a goat, rabbit, or other suitable animal and the appropriate quantity of this animal serum is mixed with the human serum of the patient to be tested.

All of the steps in the various examples herein can be conducted at room temperature, that is, in a temperature range of approximately 65°–75° F. However, temperature is not critical to my invention.

It should be understood, as has been implied hereinabove, that the description of the substrate 10 as being nonreactive with the biological particles and tagging layer applies to its chemical and biological inertness to the extent that it will not attack or destroy the biological particles, the tags, or the cleaving agent employed. The substrate must, of course, have the capability of having the first biological particles adsorb thereon as a monomolecular layer. In like manner, the material of particles 15n is nonreactive with the biological particles of layers 12 and 13 (and with substrate 10), but has the capability of binding or adhering to the layer of second biological particles 13 (or layer 12 of first particles in the absence of the second layer).

It should be apparent that the steps of the method, including the concentrating and tag-sensing steps conducted upon the cleaving agent solution collected after use are suited for use on automated, large scale testing systems.

Having described my invention with reference to particular embodiments and examples, it is believed obvious that modification and variation of my invention is possible in the light of the above teachings. Thus, a blood serum sample can be quantitatively tested for a particular biological particle in a simple variation of my invention in the following procedure. A plurality of containers of equal size are used, the size being sufficient to contain the cleaving agent solution (and rinse liquid) to be applied to one of the coated substrates to be used. Four containers and four substrates comprise a convenient number. Each substrate is exposed in the same manner to receive the same quantity of a particular first biological particle in purified form, for example, a hormone, for which the quantitative test is to be conducted. This results in the establishment of the same area monomolecular layer of the hormone on each substrate.

The blood serum sample to be assayed for this hormone is divided into four equal parts, and various known concentrations (i.e., $a$, $2a$, $4a$, $8a$) of antibody to this given hormone are respectively added to the four blood samples for complexing with some or all of the hormone in the blood serum in the separate parts of the blood sample to the extent of the concentration of antibody added. Assuming the concentrations of antibody to the hormone were properly selected, one or more of the separate parts of blood sample will now contain excess antibodies. Each of the separate parts of blood sample is then placed in contact (e.g. by immersion) with the hormone layer on a separate substrate for the same period of time. The substrates are then removed and rinsed.

The coated substrate area is next exposed to the tagging medium e.g. a method selected from the three general categories described herein. Next each substrate is contacted with an equal amount of cleaving solution (and, if necessary, rinse water). The cleaving solution and rinse used for each substrate is collected in a separate one of the containers. The four containers are then tested for radioactivity. The hormone concentration is thereby quantitatively determined as having a value between the concentrations ($a$, $2a$, $4a$, $8a$) at which substantial radiation is first detected and the next lower concentration.

It is, therefore, to be understood that changes may be made in a particular embodiment of my invention as described which are within the full intended scope of the invention as defined by the following claims.

What I claim as new and desire to secure by Letters Patent of the United States is:

1. A diagnostic method for determining the presence or absence of select biological particles in a liquid sample comprising the steps of:

contacting surface area of a substrate with first biological particles, said first biological particles being specific to the select biological particles and being dispersed as a first layer coating said surface area;

contacting the coated surface area of said substrate with the sample liquid for a preselected period of time;

applying a tagging medium to the coated surface area resulting from the preceding step, said tagging medium making tags available to said coated surface area;

contacting the coated surface area resulting from the preceding step with a cleaving agent solution, said cleaving agent solution being capable of selectively destroying such bonding as may exist between said first biological particles and select biological particles;

separating from said substrate the cleaving agent solution used in the preceding step together with any matter contained therein released from the coated surface area and examining said separated cleaving agent and contents thereof for the presence of emanations from the tags to indicate the presence of the select biological particles in said liquid sample.

2. The diagnostic method recited in claim 1 wherein the substrate is substantially planar.

3. The diagnostic method recited in claim 1 wherein the substrate is non-planar.

4. The diagnostic method recited in claim 1 wherein the surface area of the substrate contacted with the first biological particles is metallic.

5. The diagnostic method recited in claim 1 wherein the surface area of the substrate contacted with the first biological particles is non-metallic.

6. The diagnostic method recited in claim 1 wherein the first biological particles are protein.

7. The diagnostic method recited in claim 6 wherein the first biological particles are antigen.

8. The diagnostic method recited in claim 6 wherein the first biological particles are antibody to the select biological particles.

9. The diagnostic method recited in claim 1 wherein the select biological particles are cellular.

10. The diagnostic method recited in claim 1 wherein the select biological particles are viruses.

11. The diagnostic method recited in claim 1 wherein the select biological particles are bacteria.

12. The diagnostic method recited in claim 1 wherein the tagging medium contains a composition chemically reactive with biological particles for direct tagging thereof.

13. The diagnostic method recited in claim 1 wherein the tagging medium contains third biological particles specifically reactive with the select biological particles, said third biological particles having been directly tagged prior to being applied to the coated surface.

14. The diagnostic method recited in claim 1 wherein the tagging medium contains adherent, nonreactive non-biological pre-tagged particles.

15. The diagnostic method recited in claim 14 wherein the nonreactive pre-tagged particles are applied as a layer by lightly spraying an aerosol thereof over the coated surface.

16. The diagnostic method recited in claim 1 wherein the tags emit radiation.

17. The diagnostic method recited in claim 16 wherein the tags are radioactive.

18. The diagnostic method recited in claim 16 wherein the tags are fluorescent.

19. The diagnostic method recited in claim 1 wherein the cleaving agent solution is a weak acid solution.

20. The diagnostic method recited in claim 19 wherein the pH of the weak acid solution is in the range of 1-5.

21. The diagnostic method recited in claim 1 wherein the cleaving agent solution is an alkaline solution.

22. The diagnostic method of claim 21 wherein the pH of the alkaline solution is in the range of 9-13.

23. The diagnostic method recited in claim 1 wherein the cleaving agent solution is a concentrated salt solution.

24. The diagnostic method of claim 1 further comprising the steps in which after the coated surface area is contacted with cleaving agent solution, said coated surface area is rinsed and both the cleaving agent solution and the rinse are collected and used for the subsequent examining step.

25. The diagnostic method of claim 1 further comprising the step of concentrating the cleaving agent solution used together with any matter contained therein after separation from the substrate and before the examining step.

26. The diagnostic method of claim 1 further comprising the step of examining the coated surface area of the substrate for tag emanations prior to contacting said area with cleaving agent solution.

27. The diagnostic method of claim 14 wherein the nonreactive pre-tagged particles are applied over the coated surface area and form a porous, opaque layer.

28. The diagnostic method recited in claim 15 wherein the layer is opaque.

29. The diagnostic method of claim 12 wherein the composition is radioactive.

30. The diagnostic method of claim 29 wherein the composition contains $^{125}$I.

31. The diagnostic method of claim 12 wherein the composition is fluorescent.

* * * * *